(12) United States Patent
White et al.

(10) Patent No.: US 6,495,512 B1
(45) Date of Patent: Dec. 17, 2002

(54) SALICYLALDEHYDE-CONTAINING COMPOSITION HAVING ANTIMICROBIAL AND FRAGRANCING PROPERTIES AND PROCESS FOR USING SAME

(75) Inventors: Michael John Robert White, Amsterdam (NL); Maria Therese Lis-Balchin, London (GB); Elisabeth J. M. Simpson, South Ayrshire (GB); Stanley G. Deans, South Ayrshire (GB); Remco Johannes Hendrik De Meijere, Huizen (NL)

(73) Assignees: International Flavors & Fragrances Inc., New York, NY (US); South Bank University Enterprises Ltd. (GB); Cosar Ltd. (GB)

( * ) Notice: Subject to any disclaimer, the term of this patent is extended or adjusted under 35 U.S.C. 154(b) by 405 days.

(21) Appl. No.: 09/603,454

(22) Filed: Jun. 23, 2000

(51) Int. Cl.$^7$ ................................................. A61K 7/46
(52) U.S. Cl. ............................. 512/22; 512/8; 512/20; 512/23; 512/25; 512/26; 512/27; 424/76.8; 424/405; 422/1; 422/28; 422/36
(58) Field of Search ............................... 512/8, 20, 22, 512/23, 25, 26, 27; 424/76.8, 405; 422/1, 28, 36

(56) References Cited

U.S. PATENT DOCUMENTS

| | | | |
|---|---|---|---|
| 4,343,783 A | 8/1982 | Hooper et al. | 424/28 |
| 4,579,677 A | 4/1986 | Hooper et al. | 252/95 |
| 5,306,707 A | 4/1994 | Burrell et al. | 512/2 |
| 5,965,518 A | 10/1999 | Nakatsu et al. | 512/1 |
| 6,241,979 B1 | 6/2001 | Behan et al. | |

FOREIGN PATENT DOCUMENTS

WO     WO96/20714     7/1996

OTHER PUBLICATIONS

Tetsuro, et al, Abstract of Journal of the Japanese Society for Food Science and Technology, vol. 43, No. 5, 1966, pp. 535–540.

Primary Examiner—Jill Warden
Assistant Examiner—Monique T. Cole
(74) Attorney, Agent, or Firm—Arthur L. Lieberman

(57) ABSTRACT

Described are synergistic antimicrobial-fragrance compositions including broad spectrum antimicrobial compositions containing salicylaldehyde and at least one organoleptically-compatible antimicrobial synergism cofactor substance. The weight ratio range of salicylaldehyde:synergism cofactors substance is from 1:10 up to 10:1. The cofactor substance is such that the degree of synergism of the resultant mixture is defined according to the IFF Antimicrobial Synergism Test wherein the difference between the actual and expected antimicrobial values of the mixture is greater than or equal to a multiple of (i) 0.05 and (ii) the expected antimicrobial value of the mixture. Cofactor substances include phenolics such as cresol, caravacrol and thymol; ethyl vanillin; benzyl alcohol; indol; β-orcinol; and terpinenol-4. Microorganisms against which the synergistic compositions are effective include:

*Escherichia coli;*
*Enterococcus hirae;*
*Pseudomonas aeruginosa;*
*Staphylococcus aureus;* and
*Saccharomyces cerevisae.*

The compositions have application in all-purpose cleaning compositions, gel-type toilet rim articles, liquid-type toilet rim articles, personal shower cleaning compositions, and body and hair care products including shower gel compositions, shampoo compositions and foam bath compositions.

28 Claims, 3 Drawing Sheets

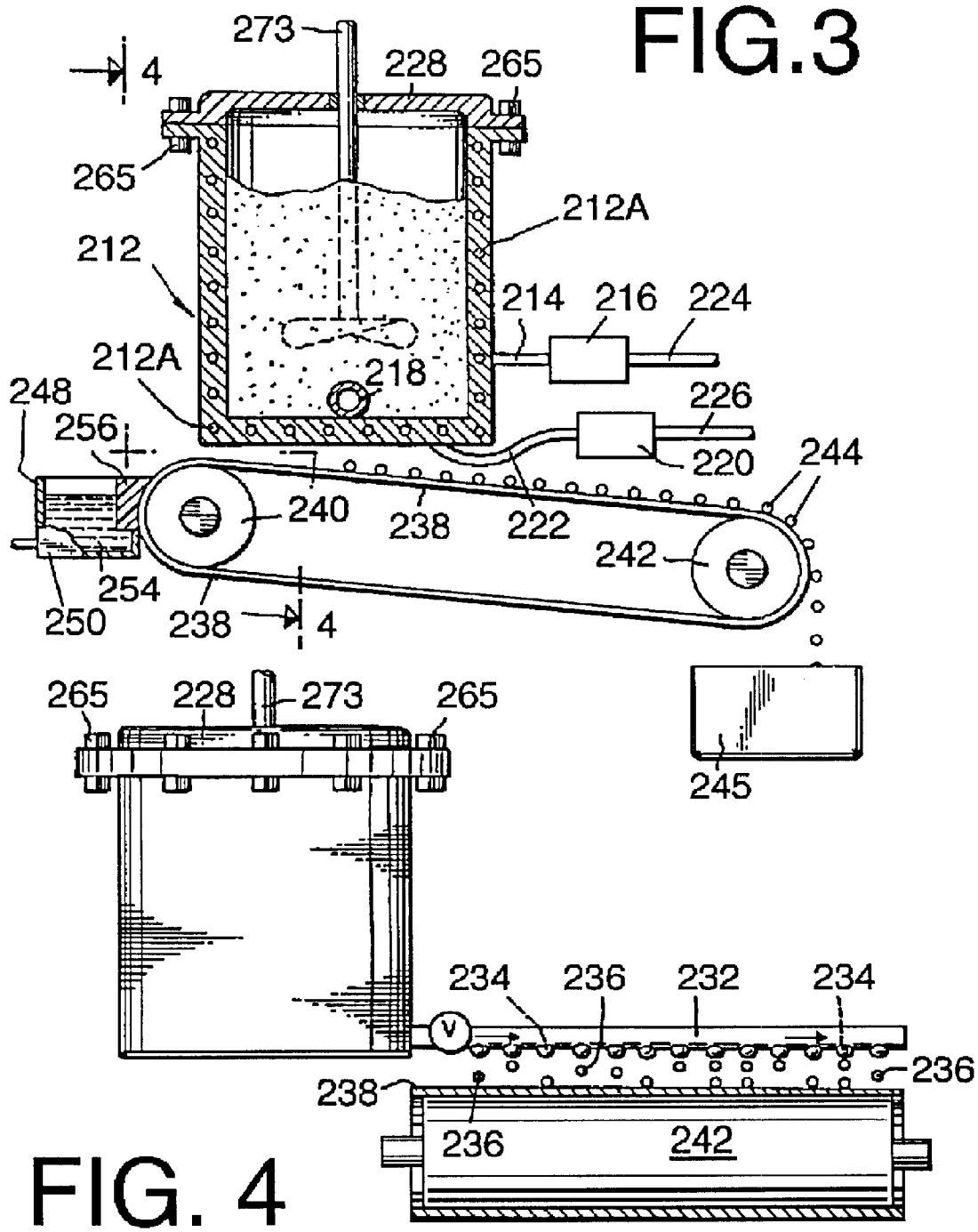

SALICYLALDEHYDE-CONTAINING COMPOSITION HAVING ANTIMICROBIAL AND FRAGRANCING PROPERTIES AND PROCESS FOR USING SAME

BACKGROUND OF THE INVENTION

The present invention relates to fragrance compositions exhibiting antimicrobial activity with a hedonically acceptable odor. The present invention also relates to antimicrobial-flavor compositions which are capable of eliminating one or more microorganisms from a solid or semisolid surface (e.g., skin) or a three-space inhabited by said microorganisms, which compositions include salicylaldehyde and at least one organoleptically compatible antimicrobial synergism cofactor substance.

The prior art, including U.S. Pat. No. 5,965,518 issued on Oct. 12, 1999, the specification for which is incorporated by reference herein, indicates that fragrances having antimicrobial activity may comprise between 3 up to 20% by weight of non-aromatic terpenoids. U.S. Pat. No. 5,965,518 further indicates that the fragrance composition may also, either alternatively or additionally, include essential oils containing phenoic compounds as a major constituent and/or essential oils containing non-aromatic terpenoids as the main constituent. U.S. Pat. No. 5,965,518 further indicates that the fragrance composition further has an odor intensity index of less than 100 and an odor evaluation acceptability index of greater than 50.

Fragrances are commonly incorporated in a wide variety of household and industrial items, for example, counter-wipes and cleansers, in order to impart a pleasing odor to a solid or semisolid surface or a three-space. A number of fragrances have been reported to have weak bacteria static activity. However, this activity has been ascertained to be too low to be of practical use. To overcome this weak activity and achieve antimicrobial fragrances of practical use either as bacteria static agents and preservatives or as bacteriacidal agents and sanitizers and disinfectants, combinations of fragrance materials with other materials are employed. For example, fragrances have been combined with a cationic phospholipid as taught in U.S. Pat. No. 5,420,104; and fragrances have been combined with a preservative and surface active agent as taught in U.S. Pat. No. 5,306,707.

Another possible way to achieve useful antimicrobial activity in fragrance compositions is to increase the effective fragrance ingredient concentration until the desired activity is achieved; for example, as described in U.S. Pat. No. 5,306,707 wherein a composition requires 30% of effective perfume ingredients in order to achieve antimicrobial activity in a household product. When using such products with such high fragrance concentrations, the aroma obtained is aesthetically displeasing and not acceptable to the consumer in the ultimate household product.

U.S. Pat. No. 5,965,518 issued on Oct. 12, 1999 attempts to overcome such objections by means of employing a mixture of 3–20% phenoic compounds and between 20–80% non-aromatic terpenoids, but does not specifically disclose the nature of the antimicrobial activity effected as a result of using such compositions and does not indicate which specific product compositions are effective against which specific microorganisms.

Accordingly, a need exists for the ability to create fragrance formulations having specific antimicrobial activity using fragrance formulations which are, in household products, capable of emitting aesthetically pleasing aromas and simultaneously, which are capable of eliminating specific microorganisms using such household products.

Nothing in the prior art sets forth fulfillment of such a need.

THE INVENTION

Our invention is directed to antmicrobial-fragrance compositions which are capable of eliminating one or more microorganisms from a solid or semisolid surface or three-space inhabited by such microorganisms. Such compositions consist essentially of (a) salicylaldehyde having the structure:

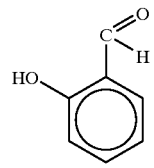

and (b) at least one organoleptically compatible antimicrobial synergism cofactor substance, with the weight ratio of salicylaldehyde:cofactor substance being from about 1:10 up to about 10:1.

The degree of synergism of the mixture is ascertained according to the "IFF Antimicrobial Synergism Test" wherein the difference between the actual an expected antimicrobial values of the mixture is greater than or equal to a multiple of 0.05 and the expected antimicrobial value of the mixture.

The IFF Antimicrobial Synergism Test is based on observation and measurement of zones of inhibition against microorganisms such as:

*Escherichia coli;*
*Enterococcus hirae;*
*Pseudomonas aeruginosa;*
*Staphylococcus aureus;* and
*Saccharomyces cerevisae.*

Such measurements of zones of inhibition may be in the form of measurement of the average radius of such zones or of the actual areas of such zones of inhibition.

The measurement of "synergism" is based on a comparison of "expected value" of the dimension of the zone of inhibition shown by the symbol: $\Delta_E$ and the actual value of the zone of inhibition shown by the symbol: $\Delta_A$. This difference: $[\Delta_A \Delta_E]$, if greater than or equal to the synergism test constant, is indicative of such synergism. The inequality is shown thusly: $\Delta_A - \Delta_E \geq K$ or, when applied to the average diameters of zones of inhibition, are shown thusly: $D_A - D_E \geq K$. The expected value of the dimension or area of the zone of inhibition is calculated according to the following generalized equation:

$$\Delta_E = \Sigma \delta_{A_i} f_{i_A} + \Sigma \delta_{B_i} f_{i_B}$$

wherein the symbol: $\delta_{A_i}$ is the zone of inhibition for a pure component; the symbol: $\delta_{B_i}$ is the zone of inhibition for a second pure component; the symbol: $f_{i_A}$ is the mole fraction or weight fraction of the first pure component in the mixture which is the subject of the synergism test; and the symbol: $f_{i_B}$ is the weight fraction or mole fraction of the second component in the mixture which is the subject of the synergism test. When multiple components are being compared against one another, the equation:

$$\Delta_E \Sigma \delta_A f_{i_A} + \Sigma \delta_B f_{i_B}$$

is used. More specifically, the calculation for the expected value as between, for example, salicylaldehyde and other components such as indole or ethyl vanillin, is according to the equation:

$$D_E = f_C D_C + f_S D_S$$

wherein the symbol: $D_E$ is the expected value of the diameter of the zone of inhibition for the mixture; the symbol: $D_C$ is the actual value of the diameter of the zone of inhibition for the pure added component; the symbol: $D_S$ is the diameter of the zone of inhibition for salicylaldehyde when used alone; the symbol: $f_C$ is the mole fraction or the weight fraction of the added component, e.g., indole or ethyl vanillin, in the mixture; and the symbol: $f_S$ is the mole fraction or weight fraction of the salicylaldehyde as used in the mixture. The expected value thus calculated, of the zone of inhibition for the mixture, is then compared with the actual value of the diameter or other dimension for the zone of inhibition according to the general inequality: $\Delta_A - \Delta_E \geq K$ or, with respect to diameters of zones of inhibition, the inequality: $D_A - D_E \geq K$. The value of K as stated, supra, for the data in the instant application, is the product of the expected value of the diameter of the zone of inhibition and 0.05 according to the equation: $K = 0.05 D_E$. However, the value of the synergism test constant in general is calculated according to the following equation: $K = (\Delta_E)\pi$ wherein the symbol: $\Delta_E$ is the expected value of the dimension of the zone of inhibition, e.g., diameter or area; and the term: $\pi$ is the "preselected confidence interval fraction," chosen, arbitrarily, in the instant application as 0.05. This value, however, may vary between 0.025 and 0.10.

The difference between actual dimension for antimicrobial inhibition and expected dimension for antimicrobial inhibition, $[\Delta_A - \Delta_E]$, and the antimicrobial/olfactory synergism test constants K, is shown by the equation: $\lambda = \{[\Delta_A - \Delta_E] - K\}$ in wherein the term: $\lambda$, is a measure of the degree of synergism. Specifically, with respect to the situation where the dimension is the diameter of the zone of inhibition, the measure of the degree of synergism is shown thusly:

$$\lambda = \{[D_A - D_E] - K\}.$$

When the measure of the degree of synergism is greater than zero, to wit: $\lambda > 0$, under the constraints of the instant specification, synergism exists. On the other hand, when the degree of synergism is less than or equal to zero, to wit: $\lambda \leq 0$, then under the constraints of the instant specification, synergism does not exist.

We have found that various cofactor substances for use in combination with salicylaldehyde having the structure:

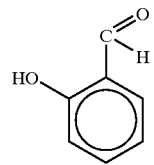

are useful in the practice of our invention, to wit:

(i) phenolic compounds having the structure:

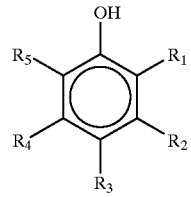

wherein one or two of $R_1$, $R_2$, $R_3$, $R_4$ and $R_5$ is the same or different $C_1-C_3$ alkyl and the other of $R_1$, $R_2$, $R_3$, $R_4$ and $R_5$ is hydrogen;

(ii) benzyl alcohol having the structure:

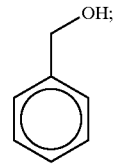

(iii) indole having the structure:

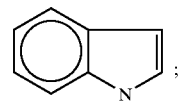

(iv) ethyl vanillin having the structure:

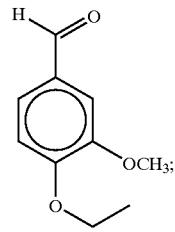

(v) orcinyl methyl ether having the structure:

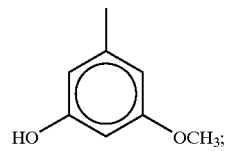

(vi) terpinenol having the structure:

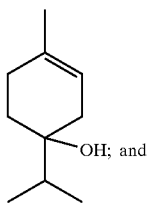

(vii) tetrahydrolinalool having the structure:

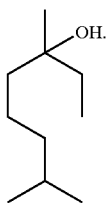

More specifically, our invention is directed, inter alia, to a composition which is a broad spectrum antimicrobial fragrance composition capable of eliminating the microorganisms:

Escherichia coli;
Enterococcus hirae;
Pseudomonas aeruginosa;
Staphylococcus aureus; and
Saccharomyces cerevisae from a solid or semi-solid surface or a three-space inhabited by such microorganisms comprising (a) salicylaldehyde having the structure:

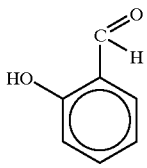

and (b) at least one organoleptically compatible antimicrobial synergism cofactor substance selected from the group consisting of:

(i) benzyl alcohol having the structure:

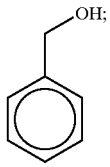

(ii) indole having the structure:

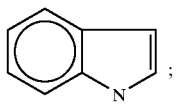

(iii) ethyl vanillin having the structure:

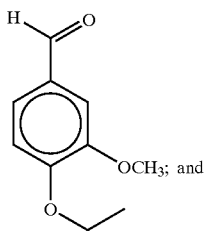

(iv) terpinenol-4 having the structure:

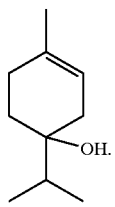

The weight ratios of salicylaldehyde:cofactor substance may vary between about 10:1 up to about 1:10, with a preferred weight ratio of 1:1.

Our invention is also directed to compositions capable of the elimination of the microorganisms:

Escherichia coli;
Pseudomonas aeruginosa;
Staphylococcus aureus; and
Saccharomyces cerevisae from a solid or semi-solid surface or three-space inhabited by such microorganisms comprising a mixture of (a) salicylaldehyde and (b) at least one organoleptically compatible antimicrobial synergism cofactor substance which is indole with the rate ratio of salicylaldehyde:indole varying from about 10:1 up to about 1:10, preferably about 1:1.

Furthermore, our invention is directed to a composition capable of eliminating the microorganism Saccharomyces cerevisae from a solid or semi-solid surface or three-space inhabited by said Saccharomyces cerevisae comprising (a) salicylaldehyde and (b) the organoleptically compatible antimicrobial synergism cofactor substance, thymol, having the structure:

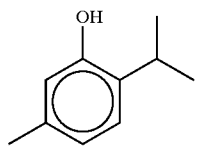

wherein the weight ratio of salicylaldehyde:thymol is from about 1:10 up to about 10:1.

Furthermore, our invention is directed to an antimicrobial-fragrance composition capable of eliminating the organisms:

Pseudomonas aeruginosa;
Staphylococcus aureus; and
Saccharomyces cerevisae from a solid or semi-solid surface or three-space inhabited by such microorganisms comprising (a) salicylaldehyde having the structure:

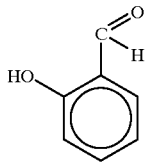

and (b) the organoleptically compatible antimicrobial synergism cofactor substance, p-cresol having the structure:

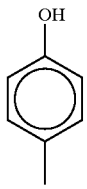

wherein the weight ratio of salicylaldehyde:p-cresol is from about 10:1 up to about 1:10.

Furthermore, our invention is directed to an antimicrobial-fragrance composition capable of eliminating the microorganisms:

*Staphylococcus aureus;* and
*Saccharomyces cerevisae* from a solid or semi-solid surface or three-space inhabited by such microorganisms comprising a mixture of (a) salicylaldehyde having the structure:

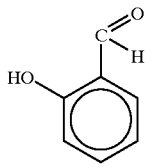

and (b) carvacrol having the structure:

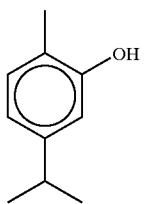

wherein the weight ratio of salicylaldehyde:carvacrol is from about 1:10 up to about 10:1.

Furthermore, our invention is directed to an antimicrobial-fragrance composition capable of eliminating the microorganisms:

*Staphylococcus aureus;* and
*Saccharomyces cerevisae* from a solid or semi-solid surface or three-space inhabited by such microorganisms comprising:
(a) salicylaldehyde;
(b) thymol;
(c) carvacrol; and
(d) p-cresol
wherein the weight ratios of salicylaldehyde:carvacrol:thymol:p-cresol is from about 1:1:1:1.

Our invention is also directed to a process for eliminating at least one of the microorganisms:

*Escherichia coli;*
*Enterococcus hirae;*
*Pseudomonas aeruginosa;*
*Staphylococcus aureus;* and
*Saccharomyces cerevisae* from a solid or semi-solid surface or three-space inhabited by such microorganisms in a microorganism-eliminating concentration and quantity, a composition which is a mixture of (a) salicylaldehyde and (b) at least one organoleptically compatible antimicrobial synergism cofactor substance selected from the group consisting of:

(i) at least one phenolic compound having the structure:

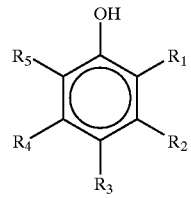

wherein one or two of $R_1$, $R_2$, $R_3$, $R_4$ and $R_5$ is $C_1$–$C_3$ alkyl and the other of $R_1$, $R_2$, $R_3$, $R_4$ and $R_5$ is hydrogen;
(ii) benzyl alcohol;
(iii) indole;
(iv) ethyl vanillin;
(v) orcinyl methyl ether having the structure:

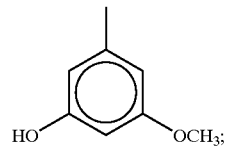

(vi) terpinenol-4 having the structure:

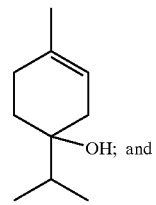

(vii) tetrahydrolinalool having the structure:

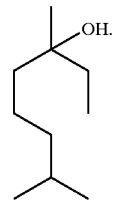

The compositions of our invention have application in all-purpose cleaning compositions, gel-type toilet rim articles, liquid-type toilet rim articles, personal shower cleaning compositions, and body and hair care products including but not limited to shower gel compositions, shampoo compositions and foam bath compositions, the formulations for which are well known to those having ordinary skill in the art.

The following substances are representative of products wherein our compositions have found significant utility and efficacy:

(i) DOVE® (tradmark of Lever Brothers Company, New York, N.Y.), moisturizing body wash, the composition for which is set forth in U.S. Pat. Nos. 5,085,857 and 5,415,810, the specifications for which are incorporated by reference herein (ingredients: water, cocamidopropyl betane, dimethacone, sodium cocoyl isethionate, sodium laureth sulfate, ammonium sulfate, laureth-4, laureth-23, titanium dioxide and guar hydroxypropyltrimonium chloride);

(ii) bagnoschiuma bath foam (contents: water, sodium laureth sulfate, sodium chloride, lauramidopropyl betaine, methylisothiazolinone and methylchloroisothiazolinone);

(iii) AJAX® (trademark of the Colgate Palmolive Company of New York, N.Y.), dish liquid; and (iv) ALBERTO VO5® (trademark of the Alberto-Culver U.S.A., Inc. Company of Melrose Park, Ill.) (contents: water, sodium lauryl sulfate, lauramide diethanolamine, sodium chloride, glycerine, retinyl palmitate, ascorbic acid, tocopheryl acetate, panthenol, ergocalciferol, corn oil, hydroxypropyl cellulose, phosphoric acid, cocamide diethanolamine, sodium laureth sulfate and DMDM hydantoin).

The compositions of our invention have also found use and are effective as antimicrobials in the formulations as exemplified in U.S. Pat. No. 5,879,666 issued on Mar. 9, 1999, the specification for which is incorporated by reference herein.

The following Table I sets forth the organoleptically compatible antimicrobial synergism cofactor substance; the microorganism(s) against which the substances are effective; and the degree of synergism of the mixture and data supporting same.

TABLE I

| Cofactor and Ratios to Salicylaldehyde | Microorganisms | k | $[D_a-D_e]$ | λ | Synergism? |
|---|---|---|---|---|---|
| Benzyl alcohol [1:1] | E. Coli | 1.26 | 11 | +9.74 | yes |
| Benzyl alcohol [1:1] | E. hirae | 0.76 | 2.2 | +1.44 | yes |
| Benzyl alcohol [1:1] | P. aeruginosa | 1.695 | 3.3 | +1.61 | yes |
| Benzyl alcohol [1:1] | S. cerevisae | 1.31 | 3.45 | +2.14 | yes |
| Benzyl alcohol [1:1] | St. aureus | 2.019 | 7.9 | +5.88 | yes |
| Indole [1:1] | E. coli | 1.46 | 10.2 | +8.74 | yes |
| Indole [1:1] | E. hirae | 0.74 | −1.05 | −1.79 | no |
| Indole [1:1] | P. aeruginosa | 1.38 | 4.1 | +2.72 | yes |
| Indole [1:1] | S. cerevisae | 1.32 | 8.35 | +7.03 | yes |
| Indole [1:1] | St. aureus | 2.002 | 4.45 | +2.45 | yes |
| Ethyl vanillin [1:1] | E. coli | 1.26 | 9.0 | +7.74 | yes |
| Ethyl vanillin [1:1] | E. hirae | 0.925 | 1.8 | +0.88 | yes |
| Ethyl vanillin [1:1] | P. aeruginosa | 1.12 | 10.7 | +9.58 | yes |
| Ethyl vanillin [1:1] | S. cerevisae | 1.2 | 19.9 | +18.70 | yes |
| Ethyl vanillin [1:1] | St. aureus | 2.055 | 10.3 | +8.25 | yes |
| Tetrahydrolinalool | E. coli | 1.31 | 11.0 | +9.69 | yes |
| Orcinyl methyl ether [1:1] | E. coli | 1.36 | 9.15 | +7.79 | yes |
| Orcinyl methyl ether [1:1] | E. hirae | 0.91 | −0.35 | −1.26 | no |
| Orcinyl methyl ether [1:1] | P. aeruginosa | 1.39 | 9.6 | +8.21 | yes |
| Orcinyl methyl ether [1:1] | S. cerevisae | 1.31 | 10.7 | +9.39 | yes |
| Orcinyl methyl ether [1:1] | St. aureus | 2.26 | 1.6 | −0.66 | no |
| Terpinenol-4 [1:1] | E. coli | 1.15 | 15.1 | +13.95 | yes |
| Terpinenol-4 [1:1] | E. hirae | 0.82 | 3.55 | +2.73 | yes |
| Terpinenol-4 [1:1] | P. aeruginosa | 1.21 | 11.1 | +9.89 | yes |
| Terpinenol-4 [1:1] | S. cerevisae | 1.15 | 14.3 | +13.15 | yes |
| Terpinenol-4 [1:1] | St. aureus | 1.90 | 14.05 | +12.15 | yes |
| p-Cresol [1:1] | E. coli | 1.58 | −2.35 | −3.93 | no |
| p-Cresol [1:1] | E. hirae | 0.99 | −2.55 | −3.54 | no |
| p-Cresol [1:1] | P. aeruginosa | 1.65 | 12.0 | +10.35 | yes |
| p-Cresol [1:1] | S. cerevisae | 1.38 | 8.7 | +7.32 | yes |
| p-Cresol [1:1] | St. aureus | 2.31 | −11.1 | −13.41 | no |
| p-Cresol [5:1] | E. coli | 1.36 | −4.88 | −6.24 | no |
| p-Cresol [5:1] | E. hirae | 0.93 | −4.00 | −4.93 | no |
| p-Cresol [5:1] | P. aeruginosa | 1.42 | 8.1 | +6.68 | yes |
| p-Cresol [5:1] | S. cerevisae | 1.14 | 7.14 | +6.00 | yes |
| p-Cresol [5:1] | St. aureus | 1.5 | 3.04 | +1.54 | yes |
| p-Cresol [10:1] | E. coli | 1.32 | (−4.08) | −5.40 | no |
| p-Cresol [10:1] | E. hirae | 1.00 | (−5.43) | −6.43 | no |
| p-Cresol [10:1] | P. aeruginosa | 1.36 | 5.04 | +3.68 | yes |
| p-Cresol [10:1] | S. cerevisae | 1.09 | 6.61 | +5.52 | yes |
| p-Cresol [10:1] | St. aureus | 1.32 | 2.8 | +1.48 | yes |
| Thymol [1:1] | E. coli | 1.51 | 1.35 | −0.16 | no |
| Thymol [1:1] | E. hirae | 0.97 | −1.35 | −2.32 | no |
| Thymol [1:1] | P. aeruginosa | 1.61 | −2.35 | −3.96 | no |
| Thymol [1:1] | S. cerevisae | 1.40 | 2.6 | +1.20 | yes |
| Thymol [1:1] | St. aureus | 2.26 | −4.1 | −6.36 | no |
| Thymol [5:1] | E. coli | 1.23 | −1.25 | −2.48 | no |
| Thymol [5:1] | E. hirae | 0.90 | −5.02 | −5.92 | no |
| Thymol [5:1] | P. aeruginosa | 1.36 | 0.59 | −0.77 | no |
| Thymol [5:1] | S. cerevisae | 1.17 | 3.84 | +2.67 | yes |
| Thymol [5:1] | St. aureus | 1.42 | −1.9 | −3.32 | no |
| Thymol [10:1] | E. coli | 1.17 | −3.8 | −4.97 | no |

TABLE I-continued

| Cofactor and Ratios to Salicylaldehyde | Microorganisms | k | [$D_a$–$D_e$] | λ | Synergism? |
|---|---|---|---|---|---|
| Thymol [10:1] | E. hirae | 0.88 | –5.69 | –6.57 | no |
| Thymol [10:1] | P. aeruginosa | 1.30 | 1.23 | –0.07 | no |
| Thymol [10:1] | S. cerevisae | 1.12 | 2.97 | +1.85 | yes |
| Thymol [10:1] | St. aureus | 1.23 | –4.08 | –5.31 | no |
| Carvacrol [1:1] | E. coli | 1.49 | 2.2 | +0.71 | yes |
| Carvacrol [1:1] | E. hirae | 0.85 | 1.15 | +0.30 | yes |
| Carvacrol [1:1] | P. aeruginosa | 1.56 | –4.5 | –6.06 | no |
| Carvacrol [1:1] | S. cerevisae | 1.45 | 5.95 | +4.50 | yes |
| Carvacrol [1:1] | St. aureus | 2.15 | 6.8 | +4.65 | yes |
| Carvacrol [5:1] | E. coli | 1.20 | –2.77 | –3.97 | no |
| Carvacrol [5:1] | E. hirae | 0.70 | –1.12 | –1.82 | no |
| Carvacrol [5:1] | P. aeruginosa | 1.27 | –2.76 | –4.03 | no |
| Carvacrol [5:1] | S. cerevisae | 1.26 | 4.19 | +2.93 | yes |
| Carvacrol [5:1] | St. aureus | 1.24 | 14.67 | +13.43 | yes |
| Carvacrol [10:1] | E. coli | 1.14 | –1.46 | –2.60 | no |
| Carvacrol [10:1] | E. hirae | 0.67 | –2.02 | –2.69 | no |
| Carvacrol [10:1] | P. aeruginosa | 1.21 | –3.87 | –5.08 | no |
| Carvacrol [10:1] | S. cerevisae | 1.21 | 2.96 | +1.75 | yes |
| Carvacrol [10:1] | St. aureus | 1.03 | 2.02 | +0.99 | yes |
| Cresol:Thymol:Carvacrol: Salicylaldehyde [1:1:1:1] | E. coli | 1.33 | 0.45 | –0.88 | no |
| Cresol:Thymol:Carvacrol: Salicylaldehyde [1:1:1:1] | E. hirae | 0.87 | –4.37 | –5.24 | no |
| Cresol:Thymol:Carvacrol: Salicylaldehyde [1:1:1:1] | P. aeruginosa | 1.41 | –0.37 | –1.78 | no |
| Cresol:Thymol:Carvacrol: Salicylaldehyde [1:1:1:1] | S. cerevisae | 1.24 | 2.43 | +1.19 | yes |
| Cresol:Thymol:Carvacrol: Salicylaldehyde [1:1:1:1] | St. aureus | 1.6 | 2.2 | +0.60 | yes |

We have also ascertained a relationship to the molecular weight of the organoleptically compatible antimicrobial synergism cofactor substance used in admixture with the salicylaldehyde in the compositions of our invention versus the degree of synergism, λ, and this relationship is set forth in the following Table II for *Saccharomyces cerevisae*. The following Table II is illustrated in accompanying FIG. 1, described herein briefly and in detail, infra. The plot in FIG. 1, infra, is that of the term: $\mu$ vs. λ, wherein $\mu$ is a function of the molecular weight of the cofactor, thusly described:

$$\mu = \frac{1}{10}[MW - 100]$$

wherein MW is the molecular weight of the cofactor.

TABLE II (*Saccharomyces cerevisae*)

| Cofactor Compound | $\mu$ | λ | FIG. 1 Reference Numeral |
|---|---|---|---|
| Benzyl alcohol | 0.8 | 2.14 | 15 |
| Ethyl vanillin | 8.0 | 18.70 | 11 |
| Indole | 1.7 | 7.03 | 14 |
| Terpinenol-4 | 5.4 | 13.15 | 12 |
| Thymol | 5.1 | 1.20 | 23 |
| Carvacrol | 5.1 | 4.5 | 22 |
| p-Cresol | 0.8 | 7.32 | 21 |
| Orcinyl methyl ether | 3.8 | 9.39 | 13 |

Our invention is also directed to a process for augmenting or enhancing the aroma of a consumable material selected from the group consisting of perfume compositions, colognes and perfumed articles while simultaneously imparting thereto antimicrobial properties comprising the step of admixing a consumable material base with (i) an antimicrobial-imparting quantity and concentration of a composition consisting essentially of (a) salicylaldehyde and (b) at least one organoleptically-compatible antimicrobial synergism cofactor substance with the weight ratio of salicylaldehyde:cofactor substance being from about 1:10 up to about 10:1; and (2) an aroma imparting concentration and quantity of an organoleptically-compatible perfume composition.

Such organoleptically-compatible perfume compositions consist of natural essential oils and synthetic materials. Examples of the natural and synthetic oils useful in the practice of our invention are as follows:
bitter almond;
angelica;
basil;
bergamot;
chamomile;
caraway;
celery;
citronella;
coriander;
estragon;
fennel;
ginger;
lavender;
lime;
mandarin;
melissa;
nutmeg;
bitter orange;
pepper;
peppermint;
rosemary;
spike;
valerian;
sweet almond;
anise;

bay;
cananga;
cardamom;
cinnamon;
clove;
dill;
eucalyptus;
geranium;
laurel;
lemon;
mint;
orange;
parsley;
pimento;
rose;
sage;
sassafras;
thyme; and
verbena.

The following synthetic materials are useful in the practice of our invention:
allyl amyl glycolate;
benzaldehyde;
cis-3-hexenyl acetate;
dihydromyrcenol;
n-decyl aldehyde;
methylionone;
trans,trans-δ-damascone;
β-ionone;
α-ionone;
β-damascenone;
γ-damascenone;
p-t-butyl-α-methylhydrocinnamicaldehyde;
o-t-butylcyclohexyl acetate;
i-nonyl acetate;
β-phenylethyl alcohol;
α-phenylethyl alcohol;
β-phenylethyl acetate;
β-phenylethylisobutyrate;
β-phenylethylcinnamate;
dimethylbenzylcarbinyl acetate; and
isobutylbenzoate.

The antibacterial compositions of our invention are useful in conjunction with perfume compositions in the ratio of from about 0.1% up to about 10% by weight of the perfume composition.

The antibacterial compositions of our invention are useful in conjunction with perfumed articles of our invention at a percentage of from about 0.001% up to about 5% by weight of the perfumed article, with a preferred percentage of from about 0.01% up to about 2% by weight.

Our invention is also directed to the creation of electronic data processing software designed to yield information for indication of antimicrobial synergism for a fragrance-antibacterial formulation or for a perfumed article-antibacterial formulation. The means for the creation of such software comprises:

(a) means for the ascertainment of specific antimicrobial-fragrance or perfumed article components, which individually eliminate given microorganisms on a solid or semi-solid surface or in a three-space inhabited by said microorganisms, measured by $\delta_{A_i}$ or $\delta_{V_i}$, with associated data input to the memory of a computer server;

(b) means for formulating one or more mixtures of said specific antimicrobial fragrance or perfumed article components of (a) having weight fractions or mole fractions of components, $f_{i_A}$ and $f_{i_B}$, with associated data input to the memory of a computer server;

(c) means for ascertainment of data indicative of antimicrobial activity of the mixtures of (b), $\Delta_A$, with associated data input to the memory of the computer server;

(d) means for calculation of the expected value, $\Delta_E$, of antimicrobial activity of the mixtures of (b) using the inputted, stored memory data of (a) $[\delta_{A_i}$ and $\delta_{B_i}]$ and (b) $[f_{i_A}$ and $f_{i_B}]$ according to the algorithm: $\Delta_E = \Sigma \delta_{A_i} f_{i_A} + \Sigma \delta_{B_i} f_{i_B}$;

(e) means for storing in the computer memory, the data required for calculation of k, the IFF antimicrobial/olfactory synergism test constant, which is the product of π, a preselected confidence interval fraction (e.g., a number from about 0.005 up to about 0.1, preferably 0.05 and $\Delta_E$);

(f) means for ascertainment of the difference, $[\Delta_A - \Delta_E]$, and the product, $K = {^*}\Delta_E)\pi$, with associated data input;

(g) means for instructing the setting of a system to accept a formulation in the event of: $\Delta_A - \Delta_E \geq K$ or: $\lambda > 0$, and reject a formulation in the event of: $\lambda \leq 0$, wherein, λ (the measure of the degree of synergism) is defined thusly: $\lambda = \{[\Delta_A - \Delta_E] - K\}$; and (h) means for instructing the repeating of steps (a)–(g), inclusive, in the event of a result of: $\lambda \leq 0$.

The protocols for the screenings of the organoleptically-compatible antimicrobial synergism cofactor substances, taken alone or taken in conjunction with the salicylaldehyde of our invention, are as follows:

Preparation of Microorganism Cultures:

Isosensitest agar was made by dissolving 31.4 grams of agar in 1 liter of distilled water. 10 Ml of molten agar was added to universal bottles and allowed to set at an angle to produce a slope. The bacteria were then subcultured onto the slopes individually.

Isosensitest broth was made up by dissolving 23.4 grams of powder in 1 liter of distilled water. 10 Ml of broth were then added to universal bottles.

For *Saccharomyces cerevisae,* malt extract agar (50 grams in 1 liter) and malt extract broth (20 grams in 1 liter) was used instead. The isosensitest agar and broth were autoclaved at 121° C. for 15 minutes. The malt extract agar and broth were autoclaved at 115° C. for 10 minutes.

Cells from cultures grown on the isosensitest agar and malt extract agar were inoculated the night before the agar diffusion technique was scheduled, using a sterile loop, into fresh isosensitest broth and malt extract broth and incubated overnight at 30° C. The final concentration was $10^6$ ml$^{-1}$.

Agar Diffusion Technique:

0.5 Ml of a single test microorganism was then pipetted per sterile petri dish and 20 ml amounts of molten isosensitest agar and malt extract agar at 45° C. were then added. The plates were then agitated to ensure mixing of the agar and microorganism without creating bubbles. After setting, 4 mm wells were punched in the center of each plate using a pharmacia gel punch.

Aroma chemicals at 10 μl (of pure undiluted substance as supplied, or if a solid, diluted as indicated in an appropriate volume of solvent) were applied to the wells. After 30 minutes, having allowed diffusion of the sample throughout the agar, the plates were inverted and incubated at 30° C. for 48 hours. Zones of inhibition were measured using vernier calipers. Each aroma chemical was tested in duplicate against all five microorganisms.

As olfactory agents, the antibacterial/fragrance compositions of our invention can be formulated into or used as components of a "perfume composition" or can be used as components of a "perfumed article" or the antibacterial/perfume composition may be added to perfumed articles.

The term "perfume composition" is used herein to mean a mixture of organic compounds including, for example, alcohols, aldehydes, ketones, nitrites, ethers, lactones, natural essential oils, synthetic essential oils, esters and frequently, hydrocarbons which are admixed so that the combined odors of the individual components produce a pleasant or desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation, and substances which retard evaporation; and (d) topnotes which are usually low-boiling, fresh-smelling materials.

In perfume compositions, the individual component will contribute its particular olfactory characteristics, but the overall effect of the perfume composition will be the sum of the effects of each of the ingredients. Thus, the antibacterial/perfume compositions of this invention or mixtures thereof can be used in and of themselves to alter the aroma characteristics of a perfume composition, for example, by highlighting or moderating the olfactory reaction contributed by another ingredient in the composition.

The amount of at least one of the compositions of our invention, which will be effective in perfume compositions, depends on many factors, including the other ingredients, their amounts and the effects which are desired. It has been found that perfume compositions containing as little as 0.05% of at least one of the antibacterial/perfume compositions of our invention, or even less, can be used to impart interesting herbaceous, citusy, spicy, floral, sweet and vanillin aromas with earthy, musty and green undertones to soaps, solid and liquid anionic, cationic, nonionic or zwitterionic detergents, cosmetics, powders, liquid and solid fabric softeners, optical brightener compositions and other products. The amount employed can range up to 50% or higher and will depend on considerations of cost, nature of the end product and the effect desired on the finished product and particular fragrance sought.

The antibacterial/perfume compositions of our invention can be used alone or in a perfume composition as an olfactory component in detergents and soaps; space odorants and deodorants; perfumes, colognes, toilet waters; bath salts; hair preparations such as lacquers, brilliantines, pomades and shampoos; cosmetic preparations such as creams, deodorants, hand lotions and sun screens; powders such as talcs, dusting powders, face powders; and the like.

When used as an olfactory component of a perfumed article, as little as 0.005% of one or more of the antibacterial/perfume compositions of our invention will suffice, for example, to impart an interesting herbaceous, citrusy, spicy, floral, sweet, vanillin aroma with earthy, musty and green undertones. Generally, no more than 0.5% is required. Thus, the percentage in perfumed articles of the antibacterial/perfume compositions of our invention range from 0.005% up to about 0.5% based on the weight of a perfumed article.

In addition, the antibacterial/perfume compositions of our invention can contain a vehicle or carrier for one or more of the antibacterial/perfume compositions of our invention, taken alone or taken together with other ingredients. The vehicle can be a liquid such as alcohol, such as ethanol; a glycol, such as propylene glycol; or the like. The carrier can be an absorbent solid such as a gum or components for encapsulating the composition such as gelatin which can be used to form a capsule wall surrounding the perfume/antibacterial composition as by means of coacervation, or it can be a microporous polymer onto which the antibacterial/perfume composition of our invention is adsorbed.

It will be thus apparent that one or more of the antibacterial/perfume compositions of our invention can be utilized to alter, modify, augment or enhance sensory properties, particularly organoleptic properties such as fragrances of a wide variety of consumable materials.

and wherein MW is the molecular weight of the organoleptically-compatible antimicrobial synergism cofactor for effective mixtures of salicylaldehyde:cofactor substance against *Saccharomyces cerevisae*. $\lambda$ is on the Y axis and $\mu$ is on the X axis.

Figure 2:
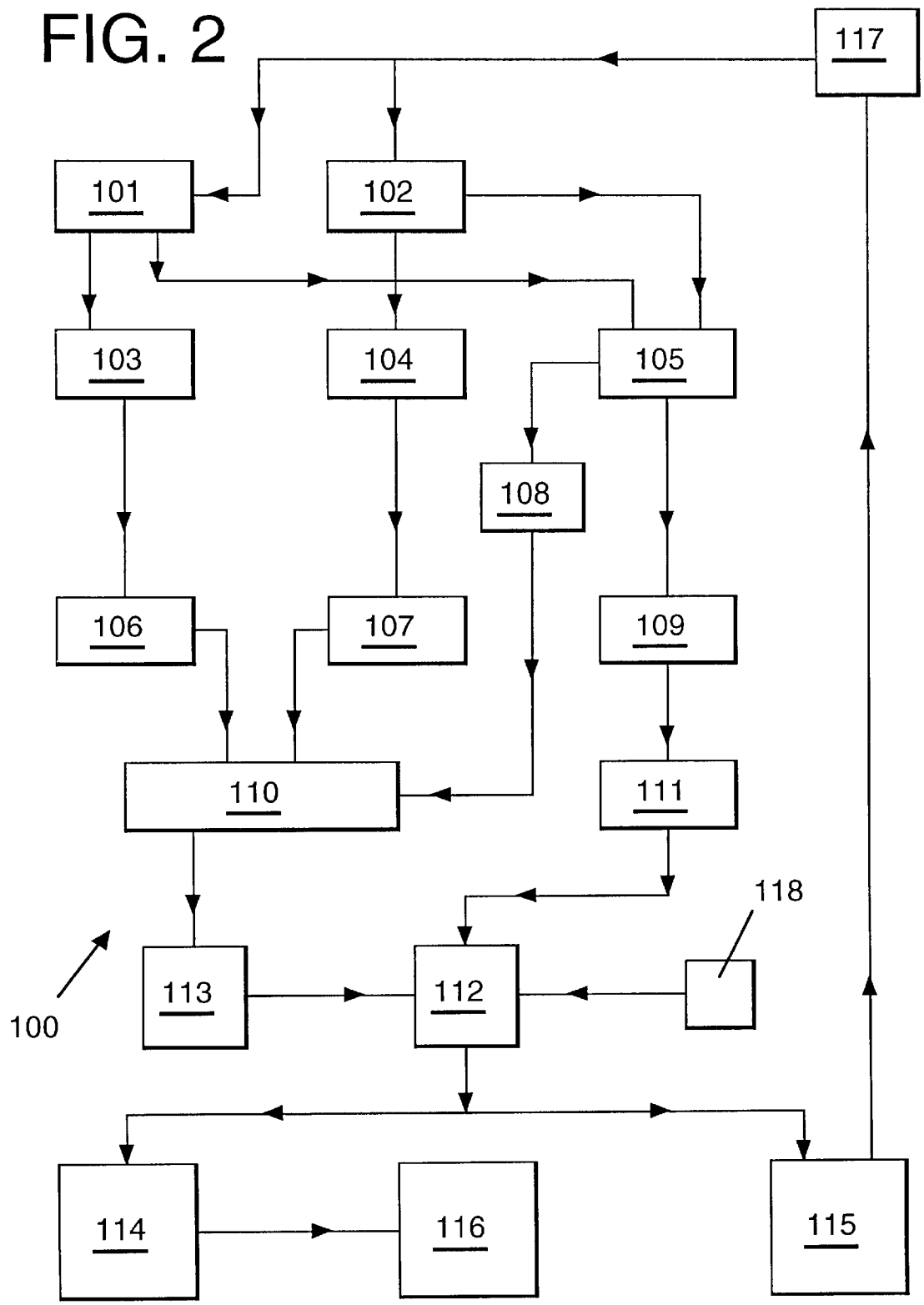

FIG. 2 is a block flow diagram showing means for the creation of electronic data processing software designed to yield information for indication of antimicrobial synergism for a fragrance-antimicrobial formulation of our invention.

FIG. 3 is a cutaway side elevation view of apparatus used in producing polymeric antibacterial/fragrance compositions containing at least one of the antibacterial/fragrance compositions of our invention.

FIG. 4 is the front elevation view of the apparatus of FIG. 3, looking in the direction of the arrows along lines 4—4 of FIG. 3.

DETAILED DESCRIPTION OF THE DRAWINGS

Figure 1:
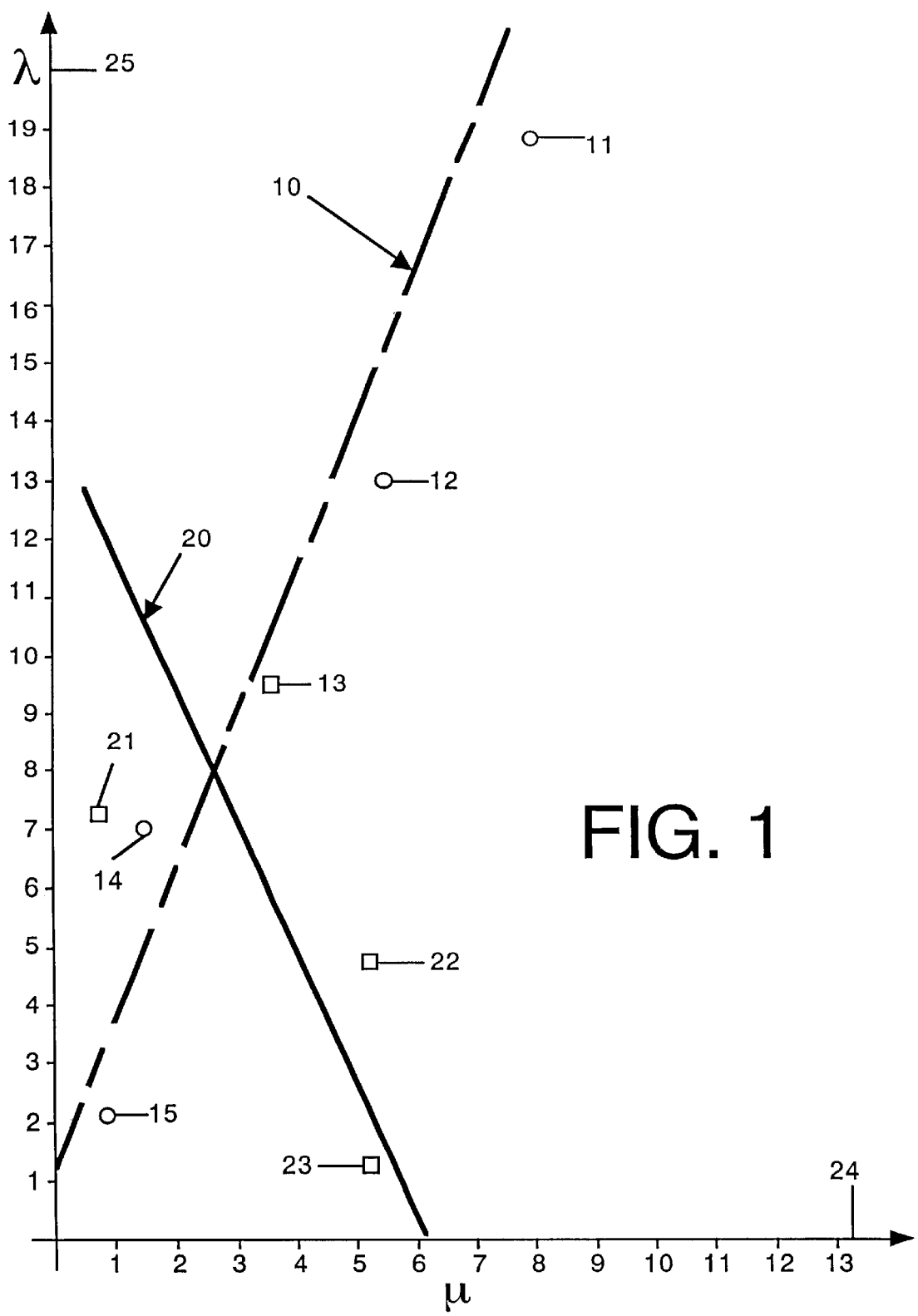
FIG. 1 is a graph of the degree of synergism ($\lambda$) vs. ($\mu$) wherein $$\mu = \frac{1}{10}[MW - 100]$$

Referring to FIG. 1, the X axis indicated by reference numeral 24, is for $\mu$, wherein $$\mu = \frac{1}{10}[MW - 100]$$

and wherein MW is the molecular weight of the organoleptically-compatible antimicrobial synergism cofactor substance used in combination (in a 1:1 weight:weight ratio) with salicylaldehyde. $\lambda$, on the Y axis, is indicated by reference numeral 25, wherein $\lambda$ is a measure of the degree of synergism indicated by the equation: $\lambda=\{[D_A-D_E]-K\}$; and wherein the term: $D_A$ is the actual diameter of the zone of antimicrobial inhibition against *Saccharomyces cerevisae* and $D_E$ is the expected value of the diameter of the zone of antimicrobial inhibition as against *Saccharomyces cerevisae* with the term: $D_E$ being calculated from the equation: $D_E=f_C D_C + f_S D_S$, wherein the term: $D_C$ is the diameter of the zone of inhibition of the cofactor substance and $D_S$ is the diameter of the inhibition zone of the pure salicylaldehyde; and wherein $f_C$ is the weight fraction of the cofactor substance in the mixure and $f_S$ is the weight fraction of salicylaldehyde in the mixture.

The graph indicated by reference numeral 10 is for the $\mu$ vs. $\lambda$ using the following cofactor substances:
benzyl alcohol;
ethyl vanillin;
indole;
terpinenol-4; and
orcinyl methyl ether.

The graph indicated by reference numeral 20 is for $\mu$ vs. $\lambda$ for the following cofactor substances:
carvacrol;
p-cresol;
thymol; and
orcinyl methyl ether.

The graph indicated by reference numeral 10 is defined according to the linear equation: $\lambda=2.5\mu+1.2$.

The data point indicated by reference numeral 11 is for a 1:1 mixture of ethyl vanilin:salicylaldehyde. The data point indicated by reference numeral 12 is for a 1:1 weight:weight mixture of salicylaldehyde:terpinenol-4.

The data point indicated by reference numeral 13 is for a 1:1 mixture of salicylaldehyde:orcinyl methyl ether. The data point indicated by reference numeral 14 is for a 1:1 weight:weight mixture of indole:salicylaldehyde. The data point indicated by reference numeral 15 is for a 1:1 weight:weight mixture of benzyl alcohol:salicylaldehyde. The data point indicated by reference numeral 21 is for a 1:1 weight:weight mixture of p-cresol:salicylaldehyde. The data point indicated by reference numeral 22 is for a 1:1 weight:weight mixture of carvacrol:salicylaldehyde. The data point indicated by reference numeral 23 is for a 1:1 weight:weight mixture of thymol:salicylaldehyde.

Referring to FIG. 2, in formulating the antimicrobial synergistic composition for creation of the fragrance-antimicrobial formulation, the first component, designated as component A, specifically, salicylaldehyde in the instant specification, is indicated by reference numeral 101. The choice of the second component, that is the organoleptically-compatible antimicrobial synergism cofactor substance(s), designated as component B, is indicated by reference numeral 102. The means for formulation of the mixture of components A and B is indicated by reference numeral 105. The testing of the neat or pure component A for antimicrobial activity and the quantum of the antimicrobial activity is indicated by reference numeral 103. The testing of the organoleptically-compatible ntimicrobial synergism cofactor substance indicated by component B is indicated by reference numeral 104. The input into computer memory of the test results from the testing operation indicated by reference numeral 103 is indicated by reference numeral 106. The inputting of data into computer memory of the test results indicated by reference numeral 104 is indicated by reference numeral 107. The inputting of the formulation and data resulting from the formulation of the mixture of components (shown in reference numeral 105) is indicated by reference numeral 108. The calculation of the expected value of the dimension of the antimicrobial zone is indicated by reference numeral 110.

The testing of the mixture of the two components indicated by A and B (for example, salicylaldehyde and indole in a 1:1 ratio) is indicated by reference numeral 109. The input into the computer memory of the actual value of the dimension of antimicrobial inhibition zone, antimicrobial inhibition zone for the mixture, $D_A$ is indicated by reference numeral 111. The input into computer memory of the value of $D_E$, the expected value of the dimension of the antimicrobial zone for the mixture is indicated by reference numeral 113. The means for instructing the ascertainment of the value of $\lambda$, the degree of synergism using the equation: $\lambda = \{[D_A - D_E] - K\}$, is indicated by reference numeral 112. The input into data memory necessary for such calculation of the term: $\pi$, which is the preselected confidence interval fraction (e.g., 0.05), is indicated by reference numeral 118.

The means for instructing the setting of the system to accept the formulation in the event of the existence of synergism, $\lambda > 0$, is indicated by reference numeral 114 and the utilization of the formulation is indicated by reference numeral 116.

The instruction for rejection of the formulation in the event of lack of synergism, $\lambda \leq 0$, is indicated by reference numeral 115.

The instruction for reformulation or rechoice of components or both in the event of rejection under the term: $\lambda \leq 0$, is indicated by reference numeral 117.

Referring to FIGS. 3 and 4, in particular, the apparatus used in producing polymeric fragrances containing at least one of the antibacterial/perfume compositions of our invention comprises a device for forming scented/antimicrobial polyolefin (for example) pellets, which comprises a vat or container 212 into which a mixture of polyolefins such as polyethylene and an aromatic/antimicrobial substance or scented/antimicrobial material is placed (e.g., a 50:50 weight:weight mixture of salicylaldehyde and indole of our invention). The container is closed by an airtight lid 228 and clamped to the container by bolts 265. A stirrer 273 traverses the lid or cover 228 in an airtight manner and is rotated in a suitable manner. A surrounding cylinder 212 having heating coils 212A, which are supplied with electric current through cable 224 from a rheostat or control 216, is operated to maintain a temperature inside the container 212, such that polyethylene or other thermoplastic polymer in the container will be maintained in the molten or liquid state. It has been found advantageous to employ a colorless, odorless polymer (e.g., polyethylene) with a viscosity ranging between 180 and 220 Saybolt seconds and having a melting point in the range of 200–280° F. The heater 212A is operated to maintain the upper portion of the container 212 within a temperature range of from 250–350° F. The bottom portion of the container is heated by means of heating coils 212A heated through a control 220 connected thereto through a connecting wire 222 to maintain the lower portion of the container within a temperature range of from 250–350° F.

Thus, polymer (e.g., polyethylene or polylactone) is added to container 212 and is heated from 10–12 hours, whereafter a scented aroma/antimicrobial property-imparting material (e.g., a 50:50 weight:weight mixture of salicylaldehyde and carvacrol of our invention) is added quickly to the melt. The material must be compatible with the polyolefin and forms a homogeneous liquid melt therewith. The scented material is of a type for the particular aroma desired and antimicrobial property desired and formulated specifically for the scenting/antimicrobial purpose for which the polyolefin will be employed.

Generally, about 1–30% by weight of the scented/antimicrobial material (e.g., a 50:50 weight:weight mixture of salicylaldehyde and indole of our invention) is added to the polyolefin.

After the scent-imparting/antimicrobial property-imparting material (e.g., a composition containing a 50:25:25 mixture of salicylaldehyde:indole:carvacrol) is added to the container 212, the mixture is stirred for a few minutes (for example, 5–15 minutes) and maintained within the temperature range as indicated previously by heating coils 212A. The controls 216 and 220 are connected, respectively, through cables 214 and 222, respectively, to heating coils 212A. The said controls 216 and 220 are also connected through cables 224 and 226. respectively, to a suitable power supply of electric current for supplying the electric power to the heating coils 212A for heating purposes.

Thereafter, the valve V is opened permitting the mass to flow outwardly through conduit 218/232 having a multiplicity of orifices 234 adjacent to the lower side thereof. The outer end of the conduit 218/232 is closed so that the liquid polymer (e.g., polyolefin) and aroma-imparting/ antimicrobial property-imparting material (e.g., a 50:25:25 mixture of salicylaldehyde:indole:p-cresol of our invention) will continuously drop through orifices 234 downwardly from conduit 232. During this time, the temperature of the polymer (e.g., polyethylene or polyolefin or polylactone) and scent-imparting/antimicrobial property-imparting material (e.g., a 50:50 weight:weight mixture of salicylaldehyde:indole of our invention) is accurately controlled so that a temperature in the range of from about 210–275° F. will exist in the conduit 218/232. The regulation of the temperature through the controls 216 and 220 is essential in order to insure temperature balance to provide for the continuous dropping or dripping of molten polymer (e.g., polyethylene) and scenting/antimicrobial-imparting material (e.g., a 50:50 weight:weight mixture of salicylaldehyde:terpinenol-4 of our invention) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 245 and utilized in processes as illustrated, infra.

A feature of this aspect of the process of our invention is the provision for moistening of the conveyor belt 238 to insure rapid formation of the solid polymeric (e.g., polyolefin or polyurethane) scented/antimicrobial-imparting pellets 244 without sticking to material which will not normally stick to a melted plastic. A moistening means 248 insures a sufficiently cold temperature of the belt surface for adequate formation of the pellets 244. The adequate moistening means comprises a container 250 which is continuously fed with water 254 to maintain a level for moistening a sponge element 256 which bears against the exterior of the belt 238.

The antibacterial/fragrance-containing polymeric pellets may be then used as is for incorporation into various products (e.g., garbage bags), or they may be further reformulated into fibers as set forth in Application for U.S. patent, Ser. No. 09/468,133 filed on Dec. 21, 1999, the specification for which is incorporated by reference herein.

The following examples serve to illustrate an embodiment of the invention as it is now preferred to practice it. It will be understood that these examples are illustrative and that the invention is to be considered restricted thereto only as indicated in the appended claims.

EXAMPLE I

Example I(A)

The perfume composition is prepared:

| Ingredients | Parts by Weight |
|---|---|
| Coumarin | 15 |
| 6-oxo-1,2,3,3,8-hexamethyl-2,3,5,6,7,8-hexahydro-1H-benz(f)-indene (50% solution in diethyl phthalate) | 60 |
| Vanillin | 2.5 |
| Myrrh coeur (50% solution in diethyl phthalate) | 5 |
| Olibanum coeur (50% solution in diethyl phthalate) | 5 |
| α-Isomethyl ionone | 30 |
| Civet tincture (10% solution in ethyl alcohol) | 10 |
| Jasmin absolute/Chassis | 40 |
| Eugenol | 10 |
| Isoeugenol | 10 |
| Rose oil, Moroccon | 50 |
| 4-(4-hydroxy-4-methylpentyl)-3-cyclohexane-10-carboxaldehyde | 15 |
| Castoreum tincture (20% solution in ethyl alcohol) | 6 |
| Styralyl acetate | 7.5 |
| Ylang extra | 5 |
| n-Heptaldehyde, dimethylacetal (10% solution in diethyl phthalate) | 10 |
| 1-hydroxy-4-t-butyl cyclohexane acetate | 20 |
| 10-undecenyl aldehyde (10% solution in diethyl phthalate) | 3 |
| 3a-Ethyl-dodecahydra-6,6,9a-trimethyl naphthol-(2,1,b)furan | 15 |
| 1,1,2,3,3-pentamethyl-6,7-dihydro-5(4H)-indanone | 5 |
| 8,9-epoxycedrane | 50 |
| Opopanax oil | 0.25 |
| GERANIOL COEUR ™ | 1.25 |
| Neroli oil | 1.25 |
| Lemon terpeneless | 2.5 |
| Rosemary French | 2.5 |
| Lavandin | 2.5 |
| Benzoin coeur | 2.5 |
| TETRAHYDRO MUGUOL ® (ref. page 2918, Perfume & Flavor Chemicals, S. Arctander II (1969) | 3.75 |
| Linalyl acetate (Hoffman La Roche) | 3.75 |
| 2-t-Butyl cyclohexanol acetate | 7.5 |
| Petitgrain oil | 15 |
| Orange oil Florida | 22.5 |
| Lemon oil California | 27.5 |
| Bergamot oil | 50 |
| Piperonyl acetate | 1.5 |
| 3-chloro-6-methyl resorcylic acid methyl ester (50% solution in diethyl phthalate) (Produced according to Example III of U.S. Pat. No. 3,729,430 issued on April 24, 1973, the specification for which is incorporated herein b reference.) | 30 |

Example I(B)

The following mixture is prepared:

| Ingredients | Parts by Weight |
|---|---|
| Salicylaldehyde | 50 |
| Indole | 50 |

5 Parts by weight of product B are admixed with 95 parts by weight of product A. The resulting material is incorporated into a soap at the level of 1.50%.

The resulting soap is effective in removing *Staphylococcus aureus* from a 10 cm in diameter area of skin washed using the soap in a standard washing procedure.

The same washing procedure imparts to the user an aesthetically pleasing aroma which lasts 5 hours following the washing procedure.

Use of the same soap composition on a solid inanimate surface (mahogany wood) having thereon a culture of *Escherichia coli* effects the elimination of said *Escherichia coli*, permanently.

EXAMPLE II

Jasmine Perfume/Antibacterial Composition

The following mixture is prepared:

| Ingredients | Parts by Weight |
|---|---|
| Benzyl acetate | 150 |
| Linalool | 60 |
| Linalyl acetate | 60 |
| Hydroxy citronellal | 60 |
| Ylang oil | 40 |
| Methyl jasmonate | 25 |
| Benzyl salicylate | 15 |
| Geranyl acetate | 25 |
| n-undecanal | 25 |
| Para-cresyl phenyl acetate | 10 |
| Phenylethyl acetate | 20 |
| Phenylethyl alcohol | 50 |
| Coumarin | 12 |
| Antibacterial/fragrance composition: | |
| salicylaldehyde; | 12 |
| indole; and | 12 |
| terpinenol-4 | 12 |

The mixture of salicylaldehyde, indole and terpinenol-4 imparts to this jasmine formulation herbaceous, citrusy, spicy, floral, sweet, earthy, musty and green undertones. Accordingly, the perfume/antimicrobial-imparting formulation of this Example II can be described as "jasmine having herbaceous, citrusy, spicy, floral, sweet, earthy, musty and green undertones."

EXAMPLE III

Preparation of a Cosmetic Powder Composition

A cosmetic powder composition is prepared by mixing in a ball mill 100 grams of talcum powder with 0.25 grams of the composition of Example II. The cosmetic powder composition has an excellent aroma which is: "jasmine having herbaceous, citrusy, spicy, floral, sweet, earthy, musty and green undertones."

EXAMPLE IV

Perfumed Liquid Detergents

Concentrated liquid detergents (lysine salt of n-dodecylbenzene sulfonic acid as more specifically described in U.S. Pat. No. 3,948,818 issued on Apr. 6, 1976, the specification for which is incorporated by reference herein) with aroma nuances as set forth in Example II are prepared containing 0.10%, 0.15%, 0.20%, 0.25%, 0.30% and 0.35% of the composition as set forth in Example II. They are prepared by adding and homogeneously admixing the appropriate quantity of the composition of Example II in the liquid detergent. The detergents all possess excellent aroma nuances as set forth in Example II.

EXAMPLE V

Preparation of Colognes and Handkerchief Perfumes

The composition as set forth in Example II is incorporated into colognes at concentrations of 2.0%/, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% in 80%, 85%, 90% and 95% aqueous food grade ethanol solutions. Distinctive and definitive aroma nuances as set forth in Example II are imparted to the colognes and to the handkerchief perfume compositions at the levels indicated.

EXAMPLE VI

Preparation of Soap Compositions

100 Grams of soap chips (per sample) (IVORY®, produced by the Procter & Gamble Company of Cincinnati, Ohio) are admixed with 1 gram of the composition of Example II until a homogeneous composition is obtained. The homogeneous composition is separated then heated under 8 atmospheres pressure at 180° C. for a period of 3 hours and the resulting liquid samples are placed in soap molds. The resulting soap cakes, on cooling, manifest excellent, long lasting aroma nuances as set forth in Example II.

EXAMPLE VII

Preparation of Solid Detergent Compositions

Detergents are prepared using the following ingredients according to Example II of Canadian Letters Patent No. 1,007,948, the specification for which is incorporated by reference herein:

| Ingredients | Parts by Weight |
|---|---|
| NEODOL ® 45-11 (a $C_{14}$—$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. A total of 100 grams each of this detergent are admixed with 0.10, 0.15, 0.20 and 0.25 grams of the composition as set forth in Example II. Each of the detergent samples has an excellent aroma as set forth in Example II.

EXAMPLE VIII

Dryer-Added Fabric Softener Article

Utilizing the procedure of Example II at column 15 of U.S. Pat. No. 3,623,396, the specification for which is incorporated by reference herein, a non-woven cloth substrate useful as a dryer-added fabric softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation:
   57%—$C_{20}$–$C_{22}$ HAPS;
   22%—isopropyl alcohol;
   20%—antistatic agent; and
   1%—of the composition of Example II.

Fabric softening compositions prepared according to Example I at column 15 of U.S. Pat. No. 3,632,396 having the aroma nuances of Example II, supra, consist of a substrate having a weight of about 3 grams per 100 square inches of substrate; a first coating located directly on the substrate coating consisting of about 1.85 grams per 100 square inches of substrate; and a outer coating coated on the first coating consisting of about 1.4 grams per 100 square inches of substrate. The composition of Example II is admixed with the outer coating mixture, thereby providing a total aromatized outer coating weight ratio to substrate of about 0.5:1 by weight of the substrate. The aroma nuances are imparted in a pleasant manner to the headspace in a dryer on operation thereof using said dryer-added fabric softener non-woven fabrics, and these aroma nuances are described in Example II, supra.

EXAMPLE IX

Hair Spray Formulations

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 Grams of the polymer is dissolved in the alcohol. The following ingredients are added to the PVP/VA alcoholic solution:

| Ingredients | Weight Percent |
| --- | --- |
| Dioctyl sebacate | 0.05 |
| Benzyl alcohol | 0.10 |
| Dow Corning 473 fluid (prepared by the Dow Corning Corporation) | 0.10 |
| TWEEN ® 20 surfactant (prepared by ICI America Corporation) | 0.03 |
| The composition as set forth in Example II. | 0.10 |

The perfume/antibacterial composition as set forth in Example II adds aroma nuances as set forth in Example II, which are rather intense and aesthetically pleasing to the users of the soft-feel, good-hold pump hair sprays.

What is claimed is:

1. An antimicrobial/fragrance composition capable of eliminating one or more microorganisms from a solid or semi-solid surface or three-space inhabited by said microorganisms consisting essentially of:
   (a) salicylaldehyde; and
   (b) at least one organoleptically-compatible antimicrobial synergism cofactor substance with the weight ratio of salicylaldehyde:cofactor substance being from about 1:10 up to about 10:1; the degree of synergism in the mixture being defined according to the IFF Antimicrobial Synergism Test, wherein the difference between the actual and expected antimicrobial values of the mixture is greater than or equal to a multiple of π and the expected antimicrobial value of the mixture and wherein π is a value of from about 0.01 up to about 0.10, wherein the cofactor is selected from the group consisting of:

(i) at least one phenolic compound having the structure:

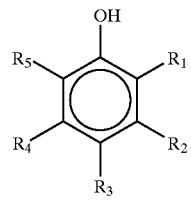

wherein one or two of $R_1$, $R_2$, $R_3$, $R_4$ and $R_5$ is the same or different $C_1$–$C_3$ alkyl and the other of $R_1$, $R_2$, $R_3$, $R_4$ and $R_5$ is hydrogen;

(ii) benzyl alcohol having the structure:

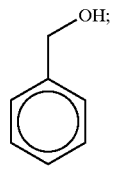

(iii) indole having the structure:

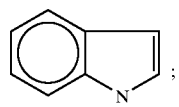

(iv) ethyl vanillin having the structure:

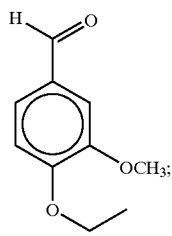

(v) orcinyl methyl ether having the structure:

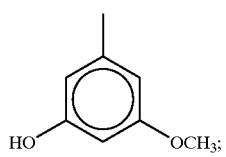

(vi) terpinenol-4 having the structure:

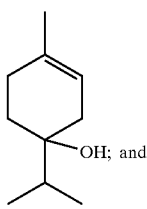

(vii) tetrahydrolinalool having the structure:

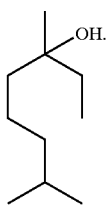

2. The composition of claim 1 which is a broad spectrum antimicrobial/fragrance formulation capable of eliminating the microorganisms:

*Escherichia coli;*
*Enterococcus hirae;*
*Pseudomonas aeruginosa;*
*Staphylococcus aureus;* and
*Saccharomyces cerevisae* from a solid or semi-solid surface or a three-space inhabited by said microorganisms wherein the cofactor substance is selected from the group consisting of:

(i) benzyl alcohol;
(ii) indole;
(iii) ethyl vanillin; and
(iv) terpinenol-4.

3. The composition of claim 1 capable of eliminating the microorganisms:

*Escherichia coli;*
*Pseudomonas aeruginosa;*
*Staphylococcus aureus;* and
*Saccharomyces cerevisae* from a solid or semi-solid surface or a three-space inhabited by said microorganisms wherein the cofactor substance is indole.

4. The composition of claim 1 capable of eliminating the microorganism, *Saccharomyces cerevisae* wherein the cofactor substance is thymol having the structure:

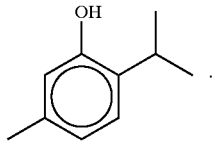

5. The composition of claim 1 capable of eliminating the microorganisms:

*Pseudomonas aeruginosa;*
*Staphylococcus aureus;* and
*Saccharomyces cerevisae* from a solid or semi-solid surface or a three-space inhabited by said microorganisms wherein the cofactor substance is p-cresol having the structure:

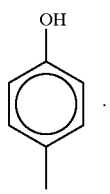

6. The composition of claim 1 capable of eliminating the microorganisms:

*Staphylococcus aureus;* and
*Saccharomyces cerevisae* from a solid or semi-solid surface or three-space inhabited by said microorganisms wherein the cofactor substance is carvacrol having the structure:

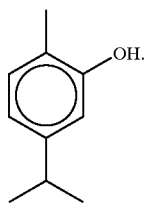

7. The composition of claim 1 capable of eliminating the microorganisms:

*Staphylococcus aureus;* and
*Saccharomyces cerevisae* from a solid or semi-solid surface or three-space inhabited by said microorganisms wherein the cofactor substance is a 1:1:1 mixture of p-cresol:thymol:carvacrol.

8. The composition of claim 1 capable of eliminating the microorganism, *Escherichia coli*, from a solid or semi-solid surface or three-space inhabited by said *Escherichia coli* wherein the cofactor substance is tetrahydrolinalool having the structure:

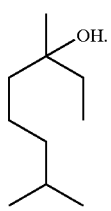

9. The composition of claim 1 capable of eliminating the microorgisms:

*Escherichia coli;*
*Enterococcus hirae;*
*Staphylococcus aureus;* and
*Saccharomyces cerevisae* from a solid or semi-solid surface or a three-space inhabited by said microorganisms wherein the cofactor substance is carvacrol having the structure:

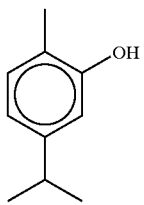

and the weight ratio of carvacrol:salicylaldehyde is 1:1.

10. A process for eliminating at least one microorganism selected from the group consisting of:
Escherichia coli;
Enterococcus hirae;
Pseudomonas aeruginosa;
Staphylococcus aureus; and
Saccharomyces cerevisae
from a solid or semi-solid surface or a three-space inhabited by said microorganisms comprising the step of applying to said surface or three-space a microorganism-eliminating concentration and quantity of the composition of matter defined according to claim 1.

11. A process for augmenting or enhancing the aroma of a consumable material selected from the group consisting of perfume compositions, colognes and perfumed articles while simultaneously imparting thereto antimicrobial properties comprising the step of intimately admixing a consumable material base with (i) an antimicrobial-imparting quantity and concentration of the composition of claim 1 and (ii) an aroma-imparting concentration and quantity of an organoleptically-compatible perfume composition, organoleptically-compatible with said antimicrobial-imparting composition.

12. A process for eliminating at least one microorganism selected from the group consisting of:
Escherichia coli;
Enterococcus hirae;
Pseudomonas aeruginosa;
Staphylococcus aureus; and
Saccharomyces cerevisae
from a solid or semi-solid surface or a three-space inhabited by said microorganisms comprising the step of applying to said surface or three-space a microorganism-eliminating concentration and quantity of the composition of matter defined according to claim 2.

13. A process for eliminating at least one microorganism selected from the group consisting of:
Escherichia coli;
Enterococcus hirae;
Staphylococcus aureus; and
Saccharomyces cerevisae
from a solid or semi-solid surface or a three-space inhabited by said microorganisms comprising the step of applying to said surface or three-space a microorganism-eliminating concentration and quantity of the composition of matter defined according to claim 3.

14. A process for eliminating at least one microorganism selected from the group consisting of:
Staphylococcus aureus; and
Saccharomyces cerevisae
from a solid or semi-solid surface or a three-space inhabited by said microorganisms comprising the step of applying to said surface or three-space a microorganism-eliminating concentration and quantity of the composition of matter defined according to claim 6 containing carvacrol having the structure:

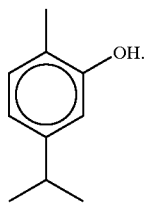

15. A process for eliminating at least one microorganism selected from the group consisting of:
Staphylococcus aureus; and
Saccharomyces cerevisae
from a solid or semi-solid surface or a three-space inhabited by said microorganisms comprising the step of applying to said surface or three-space a microorganism-eliminating concentration and quantity of the composition defined according to claim 7.

16. A process for eliminating Escherichia coli from a solid or semi-solid surface or a three-space inhabited by said Escherichia coli comprising the step of applying to said surface or three-space an Escherichia coli-eliminating concentration and quantity of the composition defined according to claim 8 comprising tetrahydrolinalool and salicylaldehyde.

17. A process for eliminating at least one microorganism selected from the group consisting of:
Escherichia coli;
Enterococcus hirae;
Staphylococcus aureus; and
Saccharomyces cerevisae
from a solid or semi-solid surface or a three-space inhabited by said microorganisms comprising the step of applying to said surface or three-space a microorganism-eliminating concentration and quantity of the composition defined according to claim 9 containing salicylaldehyde and p-cresol in the weight ratio of 1:1.

18. The process of claim 11 wherein the consumable material is a solid or liquid anionic, cationic, nonionic or zwitterionic detergent composition or soap.

19. A perfumed/antimicrobial property-imparting polymer comprising at least one microporous polymer and intimately admixed therewith in the pores thereof at least one composition defined according to claim 1.

20. A perfumed/antimicrobial property-imparting polymer comprising at least one microporous polymer and intimately admixed therewith in the pores thereof at least one composition defined according to claim 1.

21. A perfumed/antimicrobial property-imparting polymer comprising at least one microporous polymer and intimately admixed therewith in the pores thereof at least one composition defined according to claim 2.

22. A perfumed/antimicrobial property-imparting polymer comprising at least one microporous polymer and intimately admixed therewith in the pores thereof at least one composition defined according to claim 3.

23. A perfumed/antimicrobial property-imparting polymer comprising at least one microporous polymer and intimately admixed therewith in the pores thereof at least one composition defined according to claim 4.

24. A perfumed/antimicrobial property-imparting polymer comprising at least one microporous polymer and intimately admixed therewith in the pores thereof at least one composition defined according to claim 5.

25. A perfumed/antimicrobial property-imparting polymer comprising at least one microporous polymer and intimately admixed therewith in the pores thereof at least one composition defined according to claim 6.

26. A perfumed/antimicrobial property-imparting polymer comprising at least one microporous polymer and intimately admixed therewith in the pores thereof at least one composition defined according to claim 7.

27. A perfumed/antimicrobial property-imparting polymer comprising at least one microporous polymer and intimately admixed therewith in the pores thereof at least one composition defined according to claim 8.

28. A perfumed/antimicrobial property-imparting polymer comprising at least one microporous polymer and intimately admixed therewith in the pores thereof at least one composition defined according to claim 9.

* * * * *